United States Patent
Salwan

(10) Patent No.: US 7,613,620 B2
(45) Date of Patent: Nov. 3, 2009

(54) PHYSICIAN TO PATIENT NETWORK SYSTEM FOR REAL-TIME ELECTRONIC COMMUNICATIONS AND TRANSFER OF PATIENT HEALTH INFORMATION

(76) Inventor: Angadbir Singh Salwan, 10701 Balantre La., Potomac, MD (US) 20854

( * ) Notice: Subject to any disclaimer, the term of this patent is extended or adjusted under 35 U.S.C. 154(b) by 649 days.

(21) Appl. No.: 11/447,627

(22) Filed: Jun. 6, 2006

(65) Prior Publication Data
US 2006/0277075 A1  Dec. 7, 2006

Related U.S. Application Data

(60) Provisional application No. 60/687,904, filed on Jun. 7, 2005.

(51) Int. Cl.
*G06F 15/16* (2006.01)
(52) U.S. Cl. .............. 705/2; 705/3; 705/9; 600/300
(58) Field of Classification Search .......... 705/2–3, 705/9; 600/300–301
See application file for complete search history.

(56) References Cited

U.S. PATENT DOCUMENTS

| | | | |
|---|---|---|---|
| 6,272,481 B1 * | 8/2001 | Lawrence et al. ............. | 706/45 |
| 6,375,614 B1 * | 4/2002 | Braun et al. ................ | 600/300 |
| 6,757,898 B1 * | 6/2004 | Ilsen et al. ................ | 709/203 |
| 6,804,656 B1 * | 10/2004 | Rosenfeld et al. ............. | 705/3 |
| 2001/0051879 A1 * | 12/2001 | Johnson et al. ............... | 705/2 |
| 2002/0029223 A1 * | 3/2002 | Rice et al. ................ | 707/104.1 |
| 2002/0032588 A1 * | 3/2002 | Glazer et al. ................ | 705/6 |
| 2002/0042723 A1 * | 4/2002 | Rice et al. ................ | 705/2 |
| 2002/0046352 A1 * | 4/2002 | Ludwig ................ | 713/201 |
| 2003/0208108 A1 * | 11/2003 | Shewmake et al. ............. | 600/300 |
| 2005/0038692 A1 * | 2/2005 | Kane et al. ................ | 705/10 |
| 2005/0159987 A1 * | 7/2005 | Rosenfeld et al. ............. | 705/3 |
| 2005/0177400 A1 * | 8/2005 | Rosenfeld et al. ............. | 705/3 |
| 2005/0187796 A1 * | 8/2005 | Rosenfeld et al. ............. | 705/3 |
| 2005/0203777 A1 * | 9/2005 | Rosenfeld et al. ............. | 705/3 |
| 2006/0085229 A9 * | 4/2006 | Rosenfeld et al. ............. | 705/3 |
| 2007/0255584 A1 * | 11/2007 | Pavlatos et al. ............. | 705/2 |

FOREIGN PATENT DOCUMENTS

CA  2081737 A  *  5/1993
WO  WO 9524010 A1  *  9/1995

* cited by examiner

*Primary Examiner*—Gerald J. O'Connor
*Assistant Examiner*—Sind Phongsvirajati

(57) ABSTRACT

The Physician To Patient (P2P) network system, a private & secure infrastructure for independently practicing physicians and patients for real-time electronic communication & transfer of patient health information is disclosed by the invention. The invention also discloses an efficient and natural method for creation of Electronic Medical Records by physicians in their own handwriting. The P2P network system utilizes a plurality of devices and components defined by the invention, and custom programming to integrate all equipment, devices and components of the network system. The invention also discloses a highly targeted method of advertising, the One2One Advertising, for healthcare product manufacturers to reach physicians and patients. A number of healthcare related business processes, currently executed manually are performed automatically by P2P network system software. The invention will improve the quality of services to patients, and reduce the overhead cost of the medical offices, and the healthcare industry.

3 Claims, 5 Drawing Sheets

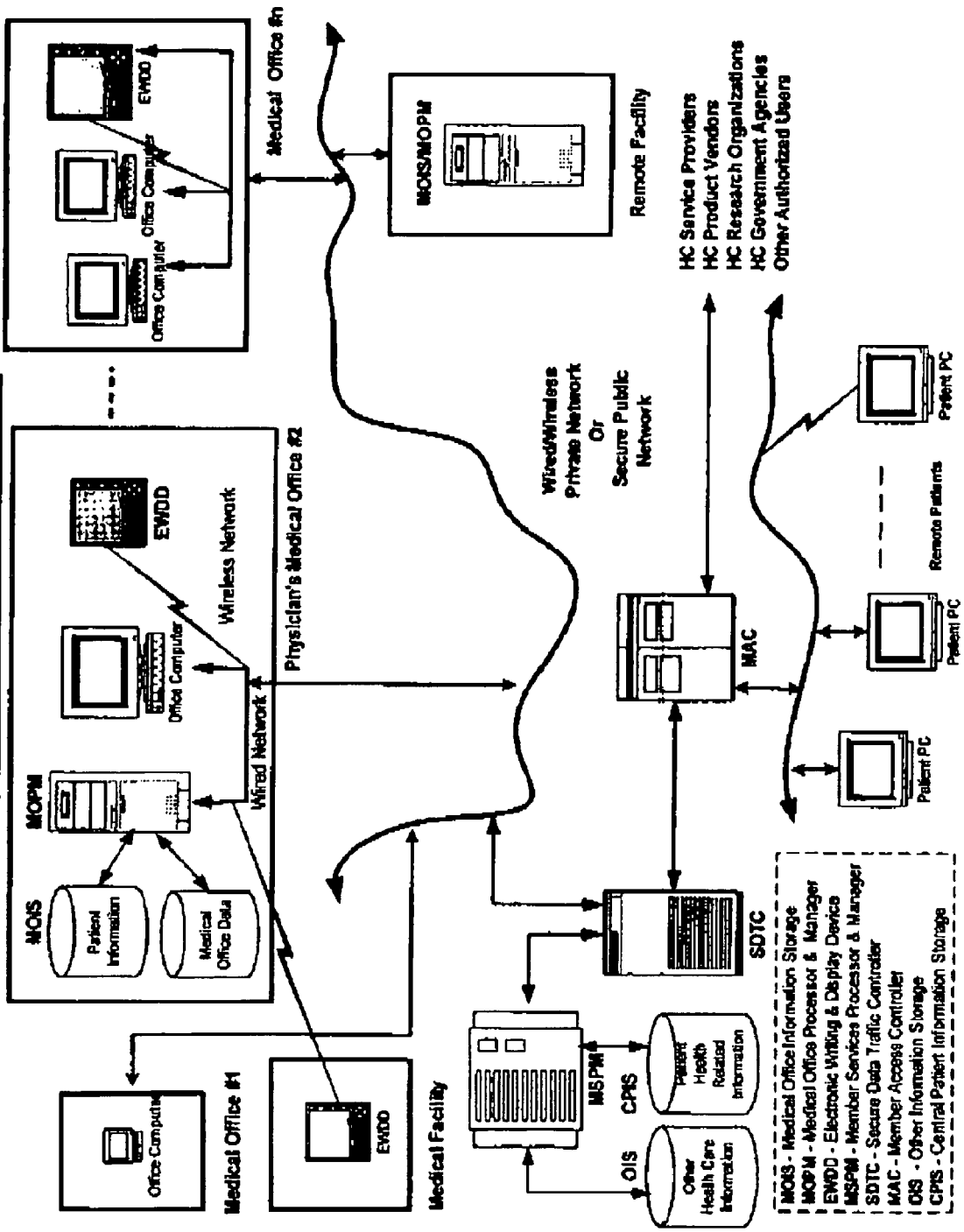

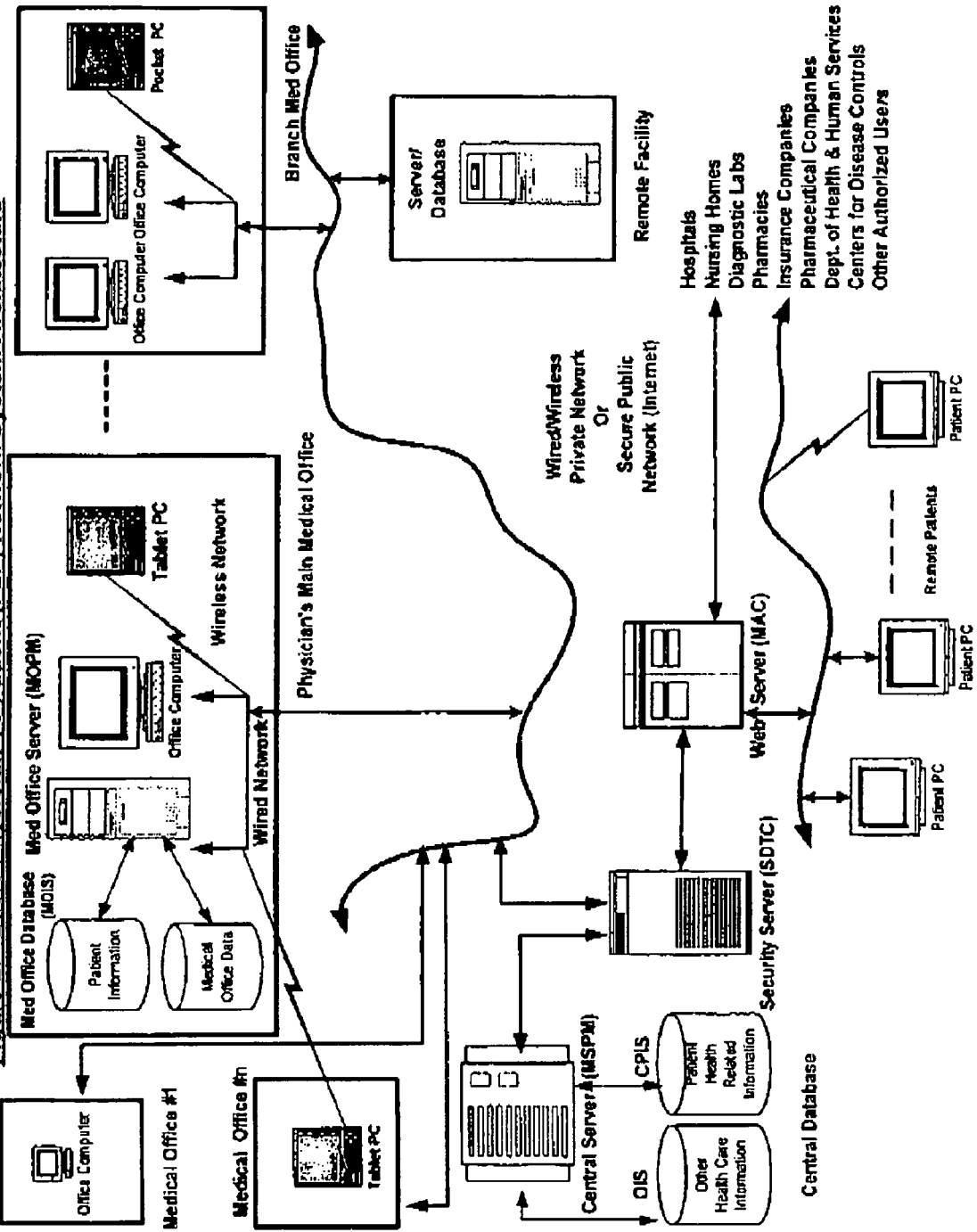

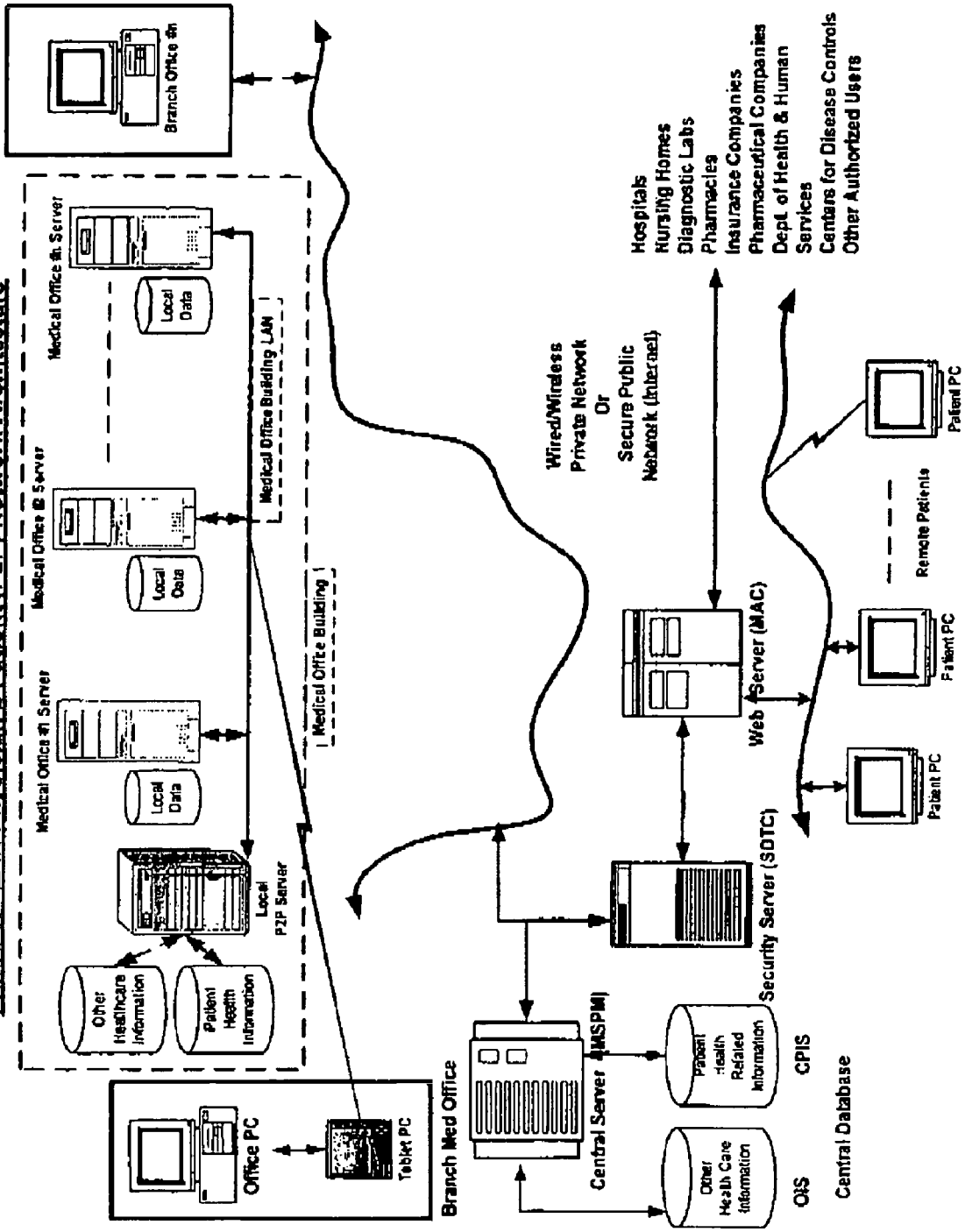

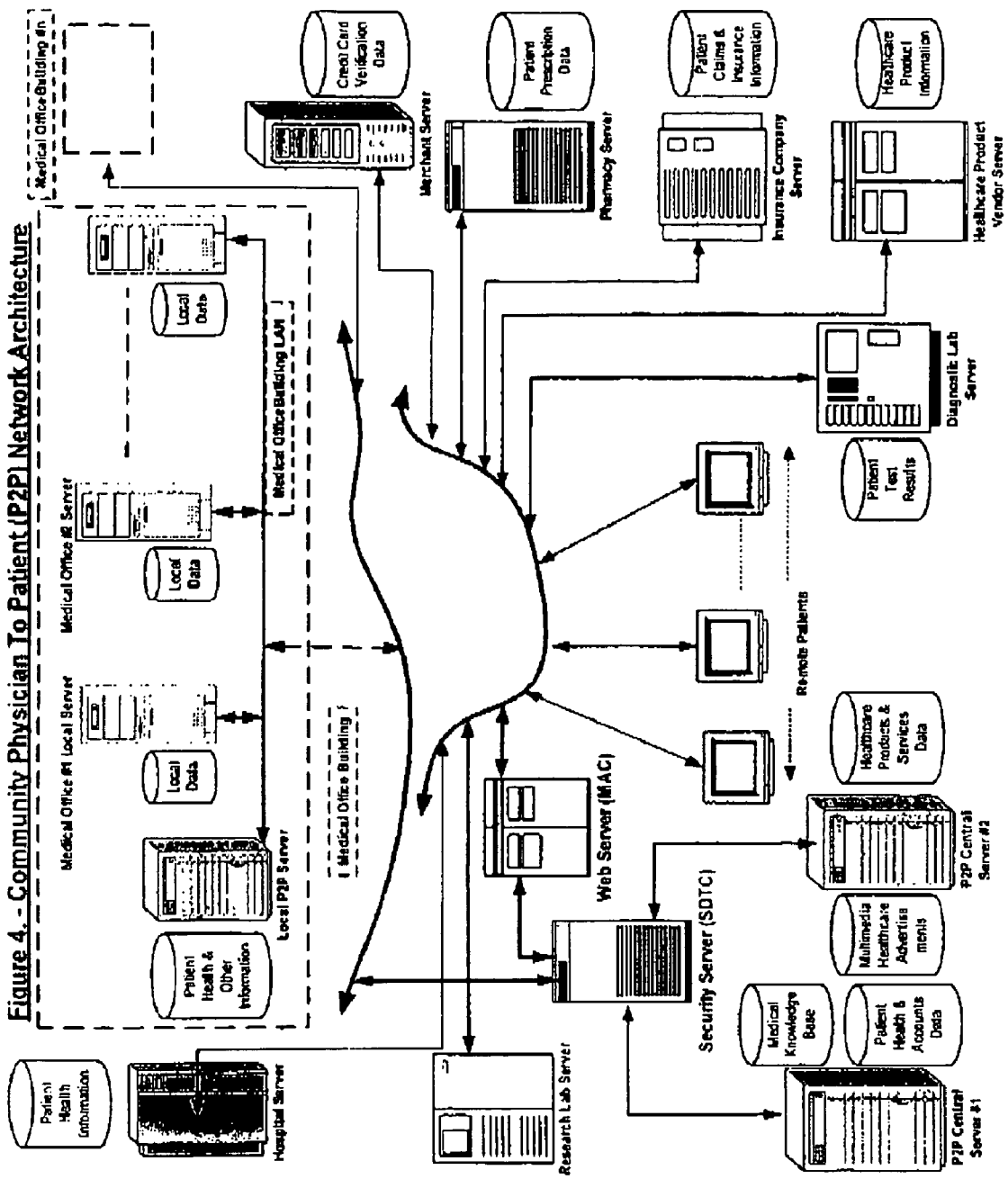

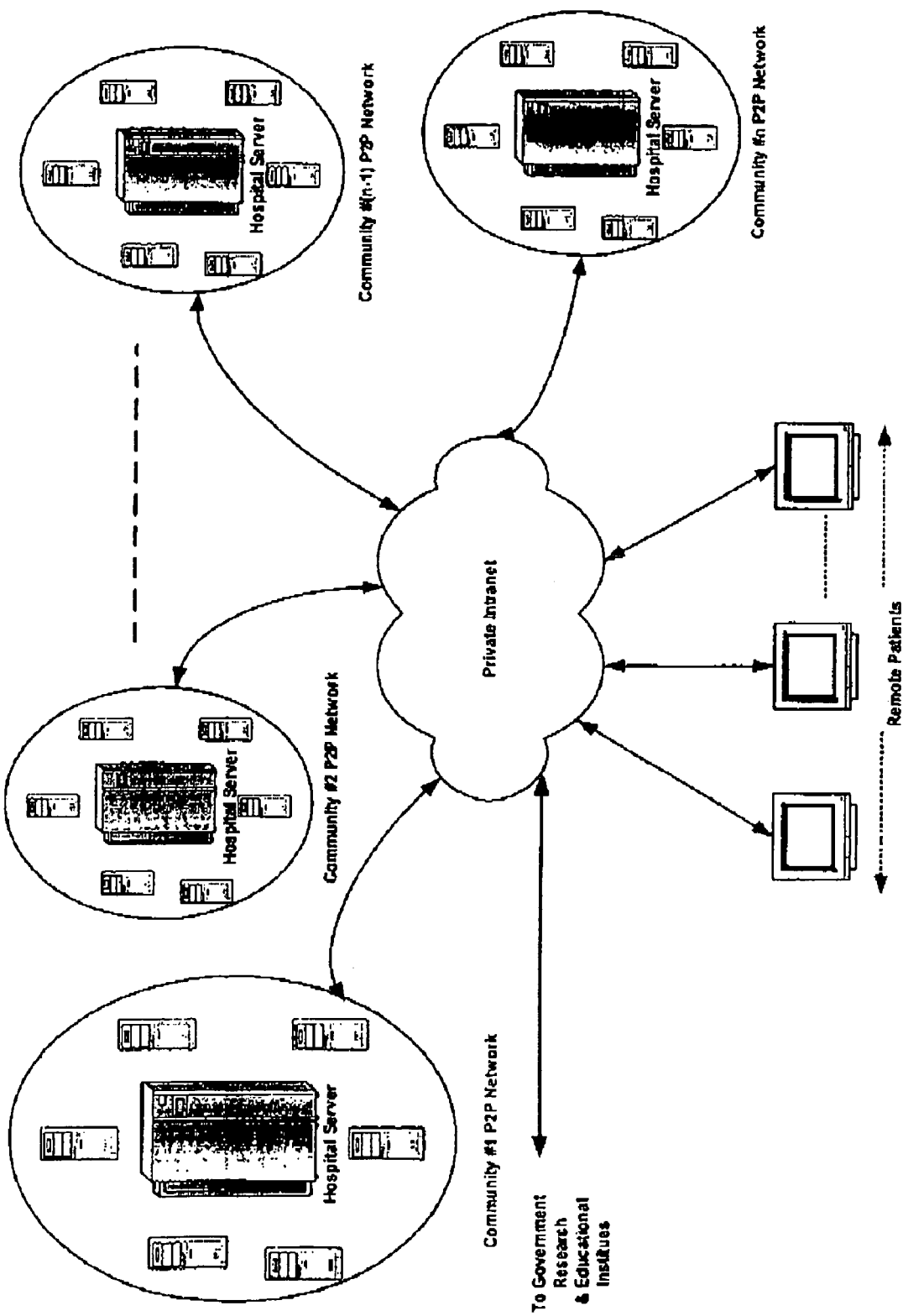

PHYSICIAN TO PATIENT NETWORK SYSTEM FOR REAL-TIME ELECTRONIC COMMUNICATIONS AND TRANSFER OF PATIENT HEALTH INFORMATION

CROSS REFERENCE TO RELATED APPLICATION

This patent application claims the benefit of the earlier filing date of, and contains subject matter related to that disclosed in the U.S. Provisional Application Ser. No. 60/687,904 filed on Jun. 7, 2005, having common inventorship, the entire contents of which being incorporated herein by reference.

U.S. Patent Documents

| | | | |
|---|---|---|---|
| 5,508,912 | Apr. 16, 1996 | Schneiderman | 705/3. |
| 5,561,446 | Oct. 1, 1996 | Montlick | 345/173. |
| 5,619,991 | Apr. 15, 1997 | Sloane | 600/300. |
| 5,713,350 | Feb. 3, 1998 | Yokota, et al. | 600/300. |
| 6,151,581 | Nov. 21, 2000 | Kraftson, et al. | 705/3. |
| 6,957,218 | Oct. 18, 2005 | Wyatt | 707/10. |

COPYRIGHT NOTIFICATION

Portions of this patent application contain materials that are subject to copyright protection. The copyright owner has no objection to the facsimile reproduction by anyone in the Patent and Trademark Office.

OTHER REFERENCES

NHII (National Health Information Infrastructure) initiative, 2001, Department of Health and Human Services NHIN (National Health Information Network) Apr. 27, 2004, National Committee of Vitals and Health Statistics www.webmd.com www.ge.com

FIELD OF THE INVENTION

The present invention relates, generally, to the field of applying Information Technology for the benefit of healthcare (HC) industry. More specifically, the present invention relates to a network system for real-time electronic communication and transfer of patient health information between physicians and patients; and among physicians, HC product suppliers, HC service providers, HC research scientists, medical educational institutes, HC related government agencies, and any other authorized healthcare related users.

BACKGROUND OF THE INVENTION

Cost-Quality Problem of Healthcare Industry

During last decade, continually rising cost of the healthcare industry has affected everybody in the country. The malpractice insurance premiums have skyrocketed, while the payments to physicians by insurance companies have continually declined. The health insurance premiums of patients have been rising steadily. The cost of drugs is increasing every year. Every HC service provider (physicians, hospitals, nursing homes, diagnostic labs etc.) is a victim of the rising cost. But it is the patient who is suffering from the rising cost and poor quality of services.

The root causes of HC industry's cost-quality problems are diverse and complex. While some problems are caused by high cost of implementing the Information Technology (IT) solutions, others are deeply embedded in the infrastructure of the U.S. healthcare industry.

Third Party Payment Related Problems

The third party (insurance companies) payment system has its merits, but it also has a number of drawbacks with the present business model utilized in the US. This system has made the HC industry an insurance-employer controlled industry rather than a market driven industry. The patient does not have the power that a customer enjoys in any market driven industry.

The employer of the patient negotiates a deal with the insurance company to select health insurance policies for its employees. Obviously, the employer looks for its own interest first, and selects the policies that are most cost effective for the employer. Since the patient (employee) does not get involved directly in the selection process, his interest is generally overlooked. Unlike a customer who has the freedom to evaluate and select a product of his choice, the patient choices are restricted.

On other side of the fence, an insurance company solely makes the decision regarding how much to pay for each medical procedure to the physician for his services. The individual physician gets no opportunity to negotiate the price with the insurance company for his services. The physician is required to sign a blanket contract, which states that he will accept whatever amount insurance company will pay him. After the physician signs the contract, the insurance companies have the authority to change the payment amounts any time.

During last decade, the payment amounts have decreased steadily. While all workers in other industries get a salary-raise every year, the physicians get a salary-cut every year. This trend is continuing with no end in sight.

Another major flaw in the system currently used in US is that all physicians receive the same amount of payment for a medical procedure irrespective of their level of experience. A fresh graduate from medical school starts his new practice, and gets paid exactly the same amount for performing a surgery as a physician with 40 years of experience. There is no provision in the payment system of insurance companies in the US to compensate a physician for his years of experience.

The roots of these problems originate from the US federal government agency—Medicare, which provides medical insurance to elderly population. Every year, the federal budget gets cut, which results in payment reduction to the physicians and other HC service providers. To make the things worst, by law, the physician cannot ask the patient to pay and makeup for the reduced payment. Since Medicare dictates its terms to the physicians, other private insurance companies follow the footsteps of Medicare, and cut the payments every year as well.

The reduction in payment to physicians (by Medicare, Medicaid and all other insurance companies), and lack of compensation for physician's experience level translates into lower quality of service to the patients. Unfortunately, majority of patients are not even aware of these problems. Since the insurance companies increase their insurance premium every year, patients expect higher quality service from the physicians. This environment results in poor physician-patient relationship.

Legal System Related Problems

The biggest legal flaw in the US healthcare industry is lack of having a cap on malpractice lawsuits, and a cap on the percentage (of pay-out) given to the attorney representing the patient. A patient can sue a physician/HC provider for almost unlimited amount even for minor issues. Since most litigation attorneys work on contingency basis, and they can keep almost the entire amount (paid by the insurance company) if the patient wins, they have strong incentive to file a lawsuit for extremely high amounts. This flaw alone has resulted in ever increasing malpractice insurance premiums of physicians.

Unfortunately, the laws are made/changed by the government body that consists of (almost) 100% attorneys. It is natural for them not to put caps on their own potential of earning millions of dollars in malpractice lawsuits.

Information Technology Related Problems

The Internet & information technologies are growing at fast speed around the world. While most other industries have adopted the latest technologies and started to harness its benefits, the HC industry (especially independently practicing physicians) has been lagging behind to adopt the state-of-the-art technology solutions. The main reasons for physicians not adopting IT solutions (currently available in the market) are the high initial cost and inefficient methods of creating Electronic Medical Records (EMRs). Majority of physicians, today, are still using basic billing software to create insurance claims, and create medical records using paper and pen, which results in high overhead cost.

Overhead Cost of Healthcare Service Providers

The methods of communication and transfer of information among independently practicing physicians, patients, HC product/service providers, and other healthcare user groups are slow and inefficient. Majority of the overhead tasks related to providing services to the patients are done manually using paper. These manually conducted operations, rising labor cost, shortage of skilled HC workers, and high turnover of employees have resulted in ever-rising overhead cost of HC services, while the quality of services to patients is deteriorating.

At present, the average overhead cost of most HC organizations is 50%. There are many factors that contribute to the higher overhead cost of HC service providers.

a) Paper Records

A basic cause of the high cost problem is the recording, storage & transfer of patient information on papers. All of these operations are very labor intensive, inefficient, and costly. To transfer information among various HC organizations (physician's office, hospital, pharmacy, diagnostic lab, and insurance company etc.), papers have to be either mailed, or faxed. By law, the HC service providers are required to keep patient records for a period of 6 years. All of these overhead operations are conducted manually, contributing to the 50% overhead cost.

b) Physician's Typing Skill

The computers have almost become a part of every business today, including medical practices. However, lacking the typing skill, majority of physicians have not been able to use them effectively. Since the physicians create patient health records, the paper remains the media of choice for majority of them. They find it convenient, efficient and cost effective to write with a pen on a paper than any other method of recording patient information.

c) Incompatible Computer Systems

Most of the HC organizations in the US, including physician's medical offices, are equipped with computers, networks and access to the Internet. These computer systems (both hardware and software) were introduced in the HC industry by different vendors during early 90s. Since the computer systems (including the Operating Systems) were evolving themselves, the IT industry was unable to create national/global standards. With the result, most of the HC organizations have computer systems that are not interoperable with each other. This incompatibility (non-interoperability) is prohibiting electronic transfer and sharing of healthcare information. Outdated medical systems software/hardware has further contributed to the incompatibility problem.

d) Isolated Healthcare Organizations

The paper records and the incompatible computer systems are the major hurdles for electronic data transfer among various HC service providers. The medical offices, even within the same building, remain isolated from each other. The manually conducted operations to transfer patient information are inefficient and labor intensive, contributing to the higher overhead cost.

With the exception of few HMOs with their own physicians and facilities, majority of the healthcare services are provided by independently practicing physicians who have small offices. These small medical offices are inter-dependent for providing healthcare services to the patients. Unless a network is created to link these small medical offices with each other, and HC information is transferred electronically, the US healthcare industry's cost-quality problem will not be solved.

e) Redundant Storage of Patient Records

Each isolated HC organization is forced to create and store its own set of patient records, mostly on papers. Thus, the same information for a patient is duplicated and stored at every HC organization. This redundant storage of patient records contributes significantly towards the high overhead cost of healthcare industry.

f) Physician to Patient Communication

Telephone is still the primary mode of communication between the patients and the medical office staff. Since physicians are busy examining the patients during office hours, a large medical office staff is needed to perform overhead tasks such as receive patient phone calls, make appointments, answering questions for patients, and take messages for physicians. Since the labor cost of medical workers is increasing every year, the overhead cost would also increase.

Paper-Based Medical Office System Work-Flow

The basic purpose of a medical office is to examine a patient, diagnose his health problem, and provide treatment. The patient examination process starts with the Primary Care physician, who provides the first level diagnosis and treatment. For simple health problems, after conducting limited diagnostic tests, the primary care physician is able to diagnose the case, and write a prescription for the appropriate medication. In a complex case, however, it requires further diagnosis. For the next level diagnosis, the patient is referred to an appropriate Specialist physician. Further tests are conducted, and treatment is provided accordingly, which may require hospitalization of the patient. For medical office visit, diagnostic testing, and providing the treatment, each healthcare service provider (physician, diagnostic lab, pharmacy, hospital, and other service providers) sends the bill to patient's insurance company. Since the patient pays part of the bill, another bill is sent to him. In some cases, patient pays his portion of the bill in the medical office before leaving the office.

The patient initiates the examination process by making a phone call to the physician's office. When the patient arrives at the medical office, he is required to fill-out a number of Registration forms (on paper), which includes his personal information, and the insurance policy related information. The registration form information is entered in the office computer by the medical staff. The medical staff also verifies patient insurance information by making a phone call to the insurance company. The physician examines the patient, and a limited number of diagnostic tests are done within the medical office. During the examination process, the physician writes notes on the patient chart (on paper). At the end of examination process, the physician writes the ICD (International Classification of Diseases) Diagnosis Codes, and the CPT (Current Procedural Terminology) Procedure codes on a pre-printed (paper) form, called the Superbill. The Patient Chart is stored in a folder and kept in a file cabinet for future reference. The office staff picks up the Superbill, and the information is entered in the billing software program of the medical office computer. A patient statement is then created by the billing software, which is given to the patient, who pays his portion of the bill and leaves the medical office. Many times, this process is completed after the patient leaves the office, and a bill is mailed to him.

After a financial transaction for the patient visit is entered in the computer, the medical office staff creates an Insurance Claim on a standard pre-printed form, called the HCFA (Health Care Financing Administration) form. This form is then mailed to the insurance company of the patient. (Many billing software programs allow submission of insurance claims electronically to a third-party, called clearinghouse, which converts the format of the electronic claim and then further submits it to the insurance company's computer.) The insurance company staff enters this information in the company's computer for further processing. Each month, the insurance company groups all the claims of the medical office, and mails one payment check to the medical office along with the description of the payment on a form called EOB (explanation of benefits). The medical staff then applies the payment to each patient's transactions, and posts the payment & the write-off amounts in his account stored in the office computer. The computer program then calculates the patient portion of the bill. This bill is printed by the medical staff, and mailed to the patient. Patient mails his payment to the medical office in the form of a check. Sometimes, the patient calls and makes the payment by his credit card. The medical staff then posts this payment to his account in the office computer.

The medical staff using paper as the media to store the information conducts the whole business process manually. Part of this information is entered in the computer for billing & accounts purposes, but papers are still needed to be stored in the medical office. By law, the medical office is required to store the patient records for a period of six years.

With the current state of the medical office business process, the overhead cost of providing healthcare services to the patients is very high, medical offices are not operating efficiently, and the quality of services to the patient is poor.

The present invention will make the current business process of a medical office more efficient, eliminate paper records, reduce the overhead cost, and improve the quality of services to the patients. This will be accomplished by automating most of the office tasks with the P2P network system software.

Marketing Cost of Healthcare Products

The HC product suppliers such as drug manufacturers have to hire highly paid marketing representatives to reach out to the physicians, educate them about the new products, and finally convince them to prescribe the new drugs to their patients. But the physicians are very busy during the day. In-between examining the patients, they have to accommodate a number of marketing representatives and listen to their brief marketing pitches. At the end of the day, it is likely that a physician may not remember which drug belongs to which representative/drug manufacturer. In many cases, the physician would even forget the name of the marketing representative.

These highly paid marketing employees have to continually struggle to get physicians' attention, and stay in front of them. The labor cost of the marketing staff is a major factor adding to the cost of HC product suppliers.

Sales Cost of Healthcare Products

The HC products, especially prescription drugs, are sold to the patients through pharmacies. The pharmacies have to add a significant mark-up (up to 300%) to the original cost of the drugs due to their own cost of sales. With the result, the patients end up paying much higher prices for the HC products.

A number of online pharmacies have popped up during last few years. But, these pharmacies are not considered reliable (and some are illegal), since the drugs are sold to the patient without recommendation/approval of his own physician.

Poor Quality of Services to Patients

1) The patient has limited choices in selecting an insurance policy, since it is the employer of the patient who makes the selection of insurance company and policies. Most patients cannot afford to buy an insurance policy as an individual, since the premiums are very high for individuals (compared to the group rates for employers).

2) The quality of services offered by physicians at Health Maintenance Organizations (HMOs) is very poor. Since the physicians are employees of the organization, or they get a flat monthly fee per patient from the insurance company, they don't have much incentive to provide better quality service. This is the root cause why most of the HMOs in the US have failed during last decade.

3) Once the employer of a patient selects an insurance company, his choices of selecting physicians are limited to those who have signed contract with the insurance company (called participating physicians). If a patient wants to get treatment from a non-participating physician, his cost is higher.

4) A patient has no means available to compare the credentials and experience of even participating physicians, as the only information provided by the insurance companies is the name, address and phone numbers of the physicians. Very few independently practicing physicians have websites where a patient could visit and get more information. Lacking this information, most patients select a physician based on the location of the medical office, or by word of mouth recommendations.

5) After receiving services, a patient does not have any means to give his feedback about the medical practice, or the physician about the quality of service, so that other patients could review his comments and make informed decisions.

6) Getting an appointment with a physician is not an easy task for the patient. He has to call during the day when medical office is open. The working patients have to call from their office to schedule an appointment. Many employers do not allow workers to do personal chores during working hours. Since most of the medical offices are very busy, a patient is put on hold for a long time. Just making an appointment can be a stressful and time-consuming task for the patient.

7) When a patient reaches a medical office for treatment, every time, he is given a set of paper forms to fill. Then he has to wait till the papers are processed before a physician can examine him. Based on a number of national level surveys, the biggest complains of patients are the waiting-time in a medical office, and repeatedly filling the paper forms.

8) A patient does not have access to his own medical records. His health related information is created by different physicians in different medical offices and hospitals, and stored locally at the HC service provider's facility. Most of this information is on papers. If a patient needs some of his information, and send a request to the medical office, it could take several days before he could receive the information.

9) By law, the HC service providers are required to keep the patient health information for 6 years. Most medical offices discard the information after 6 years to keep their maintenance costs under control. If a patient needs his information after 6 years, he is unable to obtain it.

10) Getting a referral sent to a lab or another physician's office, or a request for prescription refill from busy physicians is not an easy task for the patient. Many times, a patient has to personally go to the medical office to pick up such items.

Existing Healthcare Network Systems (Prior Art)

The leading experts in the healthcare industry, and US government leaders including senator Hillary Clinton and President Bush have recommended a number of IT solutions to solve the complex cost-quality problems of the healthcare industry. A number of healthcare IT companies offer technology solutions to all segments of the industry. However, none of the existing and proposed solutions, including a variety of networks, are capable of providing real-time electronic communication and data transfer between patients and independently practicing physicians, and among physicians, without which the cost-quality problems will not be solved.

Medical Office LAN Network Systems

Independently practicing physicians in the US have small medical offices. A number of vendors offer IT solutions that include billing and office management software. These software products run on small Local Area Networks (LAN) within the medical office where patient data is stored on a local Server. These products are designed for manual data entry by the medical office staff, and most of the overhead tasks are performed manually. Such products are designed only for office management purposes, and don't have any capabilities for real-time electronic data transfer outside the LAN network, especially to other independent medical practices.

Web-Based Medical Network Systems

Some vendors offer IT solutions to medical offices that are web-based instead of LAN based. The billing and office management software application and patient data resides on a Server outside the medical office. The staff accesses the patient data and performs all overhead functions using a web browser to connect to the Web Server. Like LAN based systems, web-based systems also lack the capability to transfer data to other independent medical practices. Another major drawback of the web-based system is that when Internet connection fails, the medical office staff is unable to perform its daily operations. Typically, the Internet Service Provider takes 1-2 days to restore the Internet connection, which can have adverse affect on the medical practice.

Web-Based Patient Records Systems

Recently, some companies have started to offer web-based services to patients where they can create, store and maintain their own health records. Physicians and other HC service providers can access and view/print the patient information through the Internet. Such systems do not have the basic capabilities to store and transfer Electronic Medical records (EMRs) created by the physicians.

Physicians Association Network Systems

Some healthcare Associations offer web based portals for the physicians and patients. These portals are primarily designed for patient education, and sometimes, allow the patients to electronically communicate with physicians. Some other services, such as Physicians Directory to find a new physician, are offered through such web-based networks. Such networks do not have any capabilities to allow physicians to create, store and transfer EMRs.

LAN-Web Combination Network Systems

A few larger vendors offer comprehensive medical office billing, accounting and management software (and hardware) packages that utilize both the LAN and web-based networks. Medical staff can access their office LAN from remote locations through the Internet, and patients are also given limited access using a web browser. These systems are designed for only one medical practice (including multiple locations of the same practice), and do not have capabilities to network with other independent medical practices.

EDI Network Systems

A number of Electronic Data Interchange (EDI) networks were introduced in the healthcare industry many years ago. Their primary objective was to submit medical claims to the insurance companies through a modem. Such networks have evolved, and now allow medical offices to send electronic claims through the Internet using a medical office billing software. These networks do not have any other networking capabilities.

Large Enterprise Network Systems

The main focus of all healthcare IT vendors is on larger HC service providers (hospitals, nursing homes, pharmacies, insurance companies etc.). These HC organizations need large IT systems for the whole enterprise, which costs millions of dollars. The IT vendors have enough financial incentives to focus on the upper-end of the HC industry, as compared to small medical practices. These enterprise systems are very sophisticated, and utilize all types of networks. Since these systems are designed for the internal use of the organization, real-time electronic communication and transfer of patient health information is restricted to physicians within the enterprise. However, some organizations do offer limited access to outside physicians and patients through the Internet.

Manual Network Systems

Majority of the medical practices in the country today are still using the manual network system for communication and transfer of patient information. Telephones, fax machines, e-mails, and postal mail is used for communication and transfer of HC information. Many times, patients personally carry their HC records from one HC provider to another. This manually operated network is responsible for high cost of the HC industry and poor quality of services to the patient.

National Health Information Infrastructure (NHII)

The initiative to create a national level health information infrastructure began in 2001 after the Anthrax terrorist activity in the US. This initiative was taken by the department of Health and Human Services (HSS), National Committee of Vitals and Health Statistics. The primary objectives of the NHII initiative were:

a) Every patient to have Personal Health records that are created and controlled by the individual or family. Such records be accessible to all HC service providers at any time from anywhere in the US.

b) To make all regional healthcare network systems within the US interoperable, and connect all networks together.

c) To make clinical data, individual health, and public health information available to all HC service providers and public health professionals in real-time for bioterrorism detection, disease prevention and healthcare research.

The NHII concept was presented to president Bush by the department of HHS. The report submitted by the national committee did not give any details about the type of the network, or the technologies to be used to create the national level network. It simply recommended the federal government to take the roll of a leader, and start a private-public initiative to build the network.

National Health Information Network (NHIN)

President Bush and his staff followed the recommendations of the National Committee of Vitals and Health Statistics, and started the initiative for the national level network on Apr. 27, 2004, Under the leadership of Mr. David J. Brailer, the Information Technology Coordinator (appointed by secretary of HHS Mr. Tommy G. Thompson), the NHII evolved to NHIN. The additional emphasis was given to encourage all HC service providers to create Electronic Health Records (EHRs) nationwide. (EHRs is another name for EMRs—the name used to define patient health information created by physicians and lab technicians.)

The goals of NHII & NHIN initiatives are quite different, and do not even address the cost-quality problem of the US healthcare industry. Implementation of NHIN will, in fact, add millions of dollars to already rising cost of HC services. Since the existing methods of creating EMRs (EHRs) are not efficient, the on-going cost of the HC industry will also keep on rising.

Existing EMR Systems (Prior Art)

For years, the information technology companies have been struggling with the problem of inefficient data entry by unskilled users. Those computer users who do not posses high-speed typing skills take a long time to enter data. Majority of physicians, today, do not have typing skills. The IT industry offers a number of solutions to the physicians for creating EMRs. However, the existing methods & EMR systems are expensive and inefficient, and therefore, majority of physicians have not adopted such EMR systems.

Dictation Systems

After examining a patient, instead of writing patient notes using paper and pen, the physician records the patient notes by speaking into a voice-recording device. His voice is digitized by the dictation system, and electronically transferred to a remote facility. A typist listens to the recorded voice, and types the patient notes into a computer. The text file is then electronically sent to the medical office, where it is proof read by the office manager, physician's assistance or the physician. Necessary corrections are made in the text, and final approved file is stored in physician's computer.

At present, the dictation system is the most commonly used EMR system in the HC industry, because it is inexpensive. However, the system has many drawbacks. It is not very efficient, and the error rate can be very high, especially if the typist cannot understand physician's accent. Proof reading and making corrections is a time consuming job, since the reader has to again listen to the recorded voice to make corrections. Integrating the text with the patient medical database is another manually performed operation. Because of these drawbacks, only a small fraction of physicians have adopted the dictation system in the country.

Voice Recognition Systems

IBM, Dragon Systems and a few other IT companies have been trying to develop voice recognition systems for over a decade. These systems have achieved some success understanding commonly used words in letter-writing etc., but in the healthcare industry, where medical terms are long and complex, the systems have not been successful. Training the voice system for each user can take up to 6 months, which further discourages the physicians to buy such systems.

Handwriting Recognition Systems

Recently, Microsoft and few other IT companies have developed handwriting recognition systems. But these systems face the same set of problems when applied in the HC industry. The physicians all over the world are known for having illegible handwriting. Therefore, the error rates of these systems are very high. With the result, they have not become popular, especially in the HC industry.

Template Based EMR Systems

Template based systems are the new wave of EMR systems in the HC industry for the last 5 years. Since the new HIPAA regulations are easy to meet if a medical office is paperless, more than 250 vendors are trying to market their products in the US. However, physicians have not welcomed these systems, as they are very expensive and inefficient. There is also a big learning curve upfront, especially if a physician is not computer literate. The template-based system is highly structured system, and forces the physician to follow a pre-defined path for recording patient notes. The physician does not have the freedom to write patient notes the way he wants. Thus, it takes him longer to complete a patient health record as compared to writing on paper. A physician will see fewer patients in a day if he uses a template based EMR system, which results in reduced revenue.

Currently, the healthcare industry in the United States is facing a very complex cost-quality problem. The P2P network system, as disclosed by the invention, is an integrated system that provides solutions to majority of the cost-quality problems.

SUMMARY OF THE INVENTION

The Physician To Patient (P2P) network system, a private & secure network system for independently practicing physicians and patients for real-time electronic communication & transfer of patient health information including clinical data is disclosed by the invention. The P2P network system also facilitates the physicians to tele-examine patients and tele-diagnose diseases from remote locations. The P2P network system also provides a private & secure infrastructure for real-time collaboration, electronic communication, exchange of patient health information, and any other healthcare related information among independently practicing physicians, patients, and other Healthcare User Groups (HC product suppliers, HC service providers, HC research scientists, medical educational institutes, HC related government agencies, and any other authorized healthcare related users). The P2P network system provides equipment, devices, methods and techniques for real-time electronic communication and data transfer among currently isolated user groups within the healthcare industry. The P2P network system utilizes state-of-the-art wired and wireless Network technologies, a plurality of devices and components defined by the invention, and custom programming to integrate all equipment, devices and components of the network system.

The invention also discloses an efficient and natural method for creation of Electronic Medical Records (EMRs) by physicians in their own handwriting, thus eliminating paper records.

The invention also discloses a highly targeted method of advertising, the One2One Advertising, for healthcare product manufacturers to reach physicians and patients at the right-time, thus helping the manufacturers to reduce their marketing and sales cost.

The invention also discloses a secure and reliable method and system for the patients to purchase medicines and other healthcare products, authorized by their personal physicians, directly from the manufacturers at discount prices.

A large number of healthcare related business processes, currently executed manually using paper, phone and fax machine are performed automatically by the P2P network system software thereby reducing the cost of healthcare industry.

P2P Network System Objectives

The main objectives of the present invention are to:

Enable electronic communication & transfer of healthcare information among physicians, patients, healthcare product & service providers, and other healthcare user groups thereby improving the productivity of healthcare industry Eliminate paper records (by creating EMRs) and related overhead cost for storage and retrieval in medical offices and other healthcare service providers' facilities Automate overhead tasks currently done manually using paper, phone and fax machine, and reduce human errors and overhead cost of independently practicing physicians' offices, and other HC service providers Enable physicians, patients, service providers and other authorized HC user groups to access patient health information, and other related information from anywhere at anytime Provide HIPAA compliant privacy for patients' personal information Provide a reliable source to the patients to purchase medicines and other healthcare products authorized by their personal physicians at discount prices Improve the quality and convenience of services to the patients, and reduce their healthcare cost

BRIEF DESCRIPTION OF THE DRAWINGS

FIG. 1. Illustrates the Physician To Patient (P2P) Network System Infrastructure.

FIG. 2. Illustrates the Basic Embodiment of Physician To Patient (P2P) Network Architecture.

FIG. 3. Illustrates the LAN Physician To Patient (P2P) Network Architecture.

FIG. 4. Illustrates the Community Physician To Patient (P2P) Network Architecture.

FIG. 5. Illustrates the Metro Physician To Patient (P2P) Network Architecture.

DETAILED DESCRIPTION OF THE INVENTION

Definitions of the Invention

The devices and components of the P2P network system, as defined by the invention, are:

P2P Network Member

A person or an organization that receives/provides healthcare services, buys/sells healthcare products, or is involved in management, or Research & Development in the healthcare industry can join the network, and become a member. A person becomes a member by electronically connecting to the network and submitting his personal and other relevant information. A username and password is issued to the member for authentication purposes.

Patients, physicians, employees of medical offices, hospitals, nursing homes, diagnostic labs, pharmaceutical companies, pharmacies, insurance companies, government agencies and research organizations are examples of P2P members.

Healthcare User Group

A group of users involved in common healthcare activities is defined as a Healthcare User Group by the invention. Examples of such user groups are physicians, hospitals, nursing homes, pharmacies, diagnostic labs, other healthcare service providers, healthcare product manufacturers, medical educational institutes and researchers, and healthcare related government agencies.

Electronic Medical Record

The Electronic Medical Record (EMR), also referenced as Electronic Health Record (EHR), is comprised of all documents related to a patient's health and created by healthcare service providers. An EMR typically includes notes written by physicians/nurses after examining the patient, diagnostic test results, copies of medical insurance card, messages exchanged among healthcare service providers, and other similar documents.

Electronic Storage Device

The Electronic Storage Device (ESD) is capable of permanently storing electronic data and information. ESD has the capability to read and write data on a medium that will not loose data if the electrical power is turned off. ESD may have a built-in controller, or use an external controller for reading & writing data and information on the permanent storage medium. Hard Disk Drive, Optical Disk Drive, Flash memory are a few examples of ESDs available in the industry at present time.

Electronic Processor & Manager

The Electronic Processor & Manager (EPM) is a system component capable of computing/processing data, and managing storage & transfer of electronic information. EPM is comprised of hardware, firmware and software components. The data processing and computing functions are, typically, performed by fixed function/programmable hardware components, while the management of data and information is accomplished by custom software. Personal Computers, workstations, and Servers are examples of EPMs available in the industry at present time.

Electronic Writing & Display Device

The Electronic Writing & Display Device (EWDD), as defined by the invention, is a device that enables a physician, or any other user, to write and display information in his own handwriting with an inkless pen. The EWDD may include temporary or permanent storage capabilities. The written information is stored and displayed in electronic form. The written information may be stored within the device, or on another storage device within the network system. The EWDD is a portable device, capable of communicating with the P2P network system through a wired, or wireless connection. The EWD is a programmable device, capable of interacting with the user. By custom programming, the EWD can become an intelligent device capable of assisting its user to improve his productivity, make better decisions, learning, and many other applications.

Intelligent Electronic Superbill

The superbill is a standard form used in a medical office to record patient's procedure codes and diagnosis codes information. This information is filled-in the superbill during a patient's visit to the physician's office. Currently, most of the physicians use a paper superbill, and hand-write the codes using an ink-pen.

The Intelligent Electronic Superbill (IES), as defined by the invention, is a form, which can be displayed on any electronic display device, such as an EWD. This form can be stored in electronic format, customized by programming, and given intelligent properties. The intelligent superbill assists the physicians in selecting the most suitable diagnosis and procedure codes.

Intelligent Patient Registration Forms

The patients typically fill paper registration forms when they visit a medical practice. Some vendors offer online forms (at their websites) to be filled by the patients. A large percentage of patients make mistakes in filling the forms, which results in denied claims by insurance companies, and in general, extra work for the medical office staff to correct the mistakes.

The Intelligent registration forms, as defined by the invention, assist the patient to correctly fill his information and prohibit him from making mistakes. The forms, typically, ask some questions to the patient. Based on his selected answers, appropriate forms are displayed step-by-step. The intelligent forms don't allow the patient to fill conflicting/wrong information thereby reducing the number of errors to a minimum.

Intelligent Appointment Forms

Intelligent appointment forms, as defined by the invention, assist the patient in making an appointment suitable for his ailment. Step by step, a number of questions are offered to the patient. Based on his answers, an appropriate appointment slot is allocated. These forms replace the medical office receptionist, who manually makes the appointment by asking a similar set of questions.

Medical Office Information Storage

The Medical Office Information Storage (MOIS) is comprised of one or more ESD components. MOIS is used in the medical office for permanently storing patient health information, and medical office business and other data and information.

Medical Office Processor & Manager

The Medical Office Processor & Manager (MOPM) is comprised of one or more EPMs. MOPM is used in the medical office for processing and management of the patient data and information, and any other data and information related to medical office business.

Member Services Processor & Manager

The Member Services Processor & Manager (MSPM) is comprised of one or more EPMs. The MSPM is used for processing and management of data and information related to P2P services provided to the network members.

Central Patient Information Storage

The Central Patient Information Storage (CPIS) is comprised of one or more ESD components. This storage component is used to store patient health information that can be utilized by HC product and service providers, and other authorized P2P members.

Other Information Storage

The Other Information Storage (OIS) is comprised of one or more ESD components. This storage component is used to store any other data and information needed to provide HC services to P2P members.

Member Access Controller

The Member Access Controller (MAC) receives all user requests for healthcare and other data/information, and checks the validity of the requesting person. Only P2P network members are allowed to send their requests to the Secure Data Traffic Controller.

Secure Data Traffic Controller

The Secure Data Traffic Controller (SDTC) controls the flow of data traffic to/from the OIS and CPIS in response to member/system requests authorized by MAC. A large P2P network system can have multiple MSPMs, and multiple OISs and CPISs. The SDTC, in this case, controls the flow of data/information to/from multiple locations.

One2One Healthcare Advertising

The One2One healthcare advertising is defined by the invention as the ability of a system to send one specific advertisement to every one specific buyer to meet his specific healthcare needs.

P2P Network System Infrastructure

FIG. 1.0 illustrates the basic infrastructure of the P2P network system disclosed by the invention. All essential devices and components needed to create a basic P2P network are illustrated in this figure. A typical small medical office of an independently practicing physician is shown as Medical Office #2, A small medical office has at least one MOPM, one MOIS, one EWDD, and one office computer connected to each other through a small local network. The physician uses an EWDD, which is connected to the office network components through a wired or wireless network connection. The EWDD can also connect to the MOPM from any outside medical facility where P2P network connection is available. The MOIS can be combined with the MOPM to work as a single system component of P2P network. In some cases, the MOIS/MOPM can be physically located outside the medical office, and accessed through the network. A large MOIS/MOPM located in a remote facility can be shared by more than one medical office.

A number of medical offices are connected to each other by a wired/wireless private network, or a wired/wireless secure public network such as Internet. Unlimited number of medical offices can be inter-connected by the P2P network. The P2P network has the capability to expand and connect to authorized network systems of HC service providers, HC product vendors, HC research organizations, HC government agencies, and any other authorized organization.

The P2P network includes at least one MAC to check and validate the identity of the users. Based on the authorization level, a member is given limited access to the data stored within the P2P network system. After validation check, MAC sends all member requests for data access to the nearest SDTC. (The P2P network may have more than one SDTC.) The SDTC controls the flow of member requests and transfer of data and information to the member computers.

The patient health related information frequently needed by P2P members is stored in the CPIS, which is shared by all P2P members. The patient health information specific to a medical practice is stored in the MOIS within the medical office. Upon request, this information can be transferred to any authorized member within the network. Other confidential medical office data, such as patient billing data, cannot be shared with outside members. Other healthcare data and information needed to perform many functions for P2P members (such as sale of discounted medicines) is stored in the OIS. All data access (from OIS and CPIS) and processing functions are performed by the MSPM. The MSPM, OIS and CPIS are located within a Data Center. A data center may have more than one MSPM, and there may be more than one data centers within the P2P network.

Basic P2P Network Architecture

The architecture of the basic embodiment of the P2P network system that can be implemented in real world is illustrated in FIG. 2. A typical medical practice, with its Main Office location and one remote Branch Office is shown in this figure. The medical practice may have more than one branch offices. The main office has a Local Server (MOPM) with a local database (MOIS), which is connected to all other Personal Computers (PCs), Tablet PCs (EWDD) and Pocket PCs (EWDD) within the main office through a wired/wireless LAN. The local database can be combined with the local Server to work as a single system component of P2P network. In some cases, the medical office Server/database can be physically located outside the medical office, and accessed through the network. A large Server/database located in a remote facility can also be shared by more than one medical office.

The Branch Office PCs and EWDDs are connected to the main office LAN through a secure public connection such as Internet. Each user logs on to the P2P network with his private and secure user ID and password. Each physician in the medical practice has a personal EWD device. When the physician is within the wireless range of the main office, his EWDD is connected to the LAN through a wireless connection. The physician carries the EWD device with him while he is in the main office, in the branch office, in the hospital, or any other location. He is able to enter and store the data in the EWDD anywhere at any time. When he comes to the main office, he can download/upload the stored data from/to his EWD device to the local Server. He can also transfer the data between his EWDD and main office Server from anywhere in the world where a network connection (such as Internet) is available.

The basic network embodiment has a Central Server (MSPM) located at an off-site Data Center facility, away from all medical offices. This Central Server provides the data access functions (from OIS and CPIS) for the whole network system. The main office Server & the PCs, the branch office PCs, and all physician EWD devices are connected to the Central Server through a secure network connection provided by the Security Server (SDTC). All patients and other P2P members can access the P2P network system from remote locations using a standard Internet browser. The Web Server (MAC) provides the member authentication functionality. However, the patients/members are given limited access to the stored data based on their assigned authentication level.

The P2P network has the capability to expand and connect to authorized healthcare networks such as hospitals, nursing homes, diagnostic labs, pharmacies, insurance companies, pharmaceutical companies, Department of Health & Human Services, Centers for Disease Controls and other authorized enterprise networks.

LAN P2P Network Architecture

The architecture of the Local Area Network (LAN), a modified embodiment of the basic P2P network system is illustrated in FIG. 3. In this embodiment, multiple medical practice offices within the same building are connected to each other, and to the Local P2P Server through a LAN network. Each medical practice has its own LAN sub-network. All sub-networks are part of the building LAN. The medical building LAN is connected to the Central Server in the Data Center through the Security Server (SDTC). Each medical practice retains its own local database for storing its confidential data.

The main advantage of the LAN embodiment is that, since the present day LAN has much higher speed as compared to WAN (Wide Area Network), certain bandwidth intensive functions, such as Videoconferencing, are feasible for physician collaboration within the building.

Community P2P Network Architecture

The architecture of the community P2P network system is illustrated in FIG. 4. This embodiment is an enhancement of the Basic, or LAN P2P network. The patients, multiple medical practices, healthcare service providers within the local community (such as hospitals, pharmacies, and diagnostic labs), the research labs, insurance companies, and the healthcare product & service providers are also connected to each other, and to the Central Servers and Databases through the Internet. Since the size of this network is large, more than one Central Servers are needed to provide all necessary functions. At least one Central Server is needed to store the patient health & accounts data, and the medical knowledge base. At least one Central Server is needed to store the healthcare product & services related data, and the multimedia advertisements & video clips related to the patient health. Each medical practice has its own patient database stored in its local Server. The enhanced version of the P2P network software will have interfaces designed to communicate with each healthcare service provider's Server to facilitate transfer of information.

Only the authorized staff of the service providers is able to view the patients' personal information. The healthcare product suppliers are connected to the network, but have limited access. The suppliers are authorized only to send their product information to the Central Server. Based on the medical condition (diagnosis codes) of each patient, the Central Server selects the appropriate healthcare product information from its stored database, and sends it to the medical office local Server. The Central Server also has the capability to send healthcare product information specifically related to the medical condition of a patient when he logs-in to the network. The medical office staff is able to send the patient information electronically to the diagnostic labs, and the staff at the lab would send the diagnostic test results to the Central Server, from where it is automatically sent to the appropriate medical practice's local Server. The research labs within the community are able to access patient data only for the purposes of conducting the research. The results of the research are sent to the Central Server by the research lab staff to be shared with other scientists, physicians and authorized staff of the healthcare product & service providers. The community P2P network is intended to provide benefits to everybody living within the community.

Metro P2P Network Architecture

The architecture of the metro P2P network system is illustrated in FIG. 5. The metro network consists of all the community networks within a metropolitan area connected to each other through the Internet, or a private network. The government and private research institutes, medical colleges, universities and other educational institutes, and any other organization related to healthcare field would be able to join the network. The Metro network is beneficial to all the people living within the metropolitan area.

Global P2P Network Architecture

In the ultimate embodiment of the network, the global Physician2Patient network system, all the metro networks are connected to each other within the United States, Canada, and possibly rest of the world. This ultimate embodiment of the P2P network will, someday, benefit the entire mankind.

Natural Method of Creating EMRs

The invention discloses a very simple and natural method of creating EMRs (also referred as EHRs). This method utilizes an EWD device, which is used by the physician or any other HC service provider. A number of EWD devices are commercially available such as a Tablet PC, Pocket PC, and many other Hand-held devices. These devices come with a pen-like component, called Stylus, which enables the user to write on a plastic surface. The plastic surface is connected to the electronic circuitry of the EWD device.

The method, as disclosed herein, allows a physician to create EMR by writing patient health related information in his own handwriting using a stylus on an EWD device. The handwritten EMR can be stored in electronic format, and viewed later by authorized medical staff, or the physician himself. A medical typist in the office, or at a remote location, can read the handwritten EMRs, and type the same information using the keyboard of a computer.

This method of creating EMRs is a natural method for the physician, since it is similar to writing on a paper with an ink-pen. Unlike other template-based EMR systems, the physician does not have any learning curve. The method is efficient, since the time taken to create a patient's Electronic Medical/Health Record is less than the template-based system. Since a physician's time costs more to the medical practice as compared to the medical typist's time, the method saves money to the medical practice. If all the physicians in the country utilize the method disclosed by the invention for creating EMRs, it can make a significant contribution in reducing the nation's healthcare cost.

P2P Network System Software

The P2P network system software integrates all the components and devices of the network, and makes them work together as a unified system. The P2P software is comprised of various modules that are custom designed, developed and installed on devices and components of P2P network. The network system software primarily controls the operation of P2P devices, components and the network itself. All user/member interfaces are defined and created with the system software. The interfaces to existing networks of HC organizations (such as hospitals, insurance companies etc.) are also created with the customized software. The P2P software provides all the functions that enable real-time electronic communication & transfer of data and patient health information among P2P members, collaboration among independently practicing physicians, automation of medical office business processes currently performed manually, and many other functions for the benefits of P2P members.

P2P Network Related Functions

The primary functions performed by the P2P system software are described below. However, the software is not limited to these functions. A number of new functions can be added to increase the capabilities of the network system.

Intelligent Appointment Scheduling

The P2P software will allow a patient to login through a secure network connection to the P2P system using his/her user name and a password. After a patient logs-in, and his identity is verified by the P2P system, he is allowed to select a medical practice, and view the schedule of all physicians within the medical practice. When he initiates the appointment scheduling process, the P2P system asks him a number of questions related to his health condition and requested appointment. Based on his answers, the system offers him the choices of appropriate appointment slots. The patient then submits his request for an appointment. The medical office staff reviews this information, and a confirmation notice about his appointment is sent to him electronically.

This function will benefit the patient as well as the physician. The patient has the freedom to make his appointment anytime from anywhere in the world. The physician saves his overhead cost, since the medical office staff is not involved in the time consuming scheduling process. The intelligent scheduling function also helps in defining the purpose of patient's visit more accurately, which results in improved billing and better documentation.

Intelligent Registration Forms

The P2P software will allow a patient to fill electronic registration, HIPAA and Medical History forms by remotely connecting to the P2P network from anywhere in the world. All patients will go to one place on P2P website to fill all the forms. These forms need to be filled only once by the patient. When a patient needs to visit any P2P member medical practice, he simply goes to the P2P website, logs-in using his ID & password, and selects the practice. His personal data, insurance policy information, medical history, and other related information automatically gets transferred to the selected practice's local Server from the P2P Central Server.

As defined by the invention, the intelligent registration forms assist the patient in correctly entering his information, and not allowing him to enter conflicting/wrong information.

The patients benefit from filling out the forms only once, and not having to wait in the waiting room for a long time. The medical practice benefits from reduced workload of its overhead staff, reduced paper records, and reduced human errors, and also helps the practice to comply with HIPAA regulations.

Waiting Room Patient Registration

For those patients who are unable to fill-out forms prior to their appointment, they will be able to visit the P2P website from a computer in the waiting room of the medical practice, and fill-out all the forms.

Electronic Patient Sign-In Sheet

When a patient arrives in the medical office, he will sign-in using a PC in the waiting room, instead of a paper sign-in sheet. This information will be stored in the local MOIS, and used for creating the electronic waiting list, and automated exam room scheduling. The electronic sign-in feature will also facilitate HIPAA compliant privacy for patients' personal information.

Waiting Room Patient Status Display

The Patient Waiting List will be displayed on a large computer screen in the waiting room. When the doctor is ready to examine a patient, he will click a check box on his EWDD, and the patient's name, doctor's name and the exam room number will be displayed in the waiting room. This information will be displayed on top part of the screen, and cover only a small area of the screen. Multimedia video clips will be displayed on rest of the screen. These video clips will be used to display educational information for the patients, advertisements sponsored by the healthcare product manufacturers, and many other types of multimedia content appropriate for the patients.

The waiting room displays will help the HC vendors in reaching the patients at the right time, i.e., when they are sick and need the products. This will help them to increase their sales and reduce the marketing cost, since such advertisements will be highly targeted and much cheaper than TV advertisements currently given by the vendors, which are broadcasted ads, and not targeted.

Automated Exam Room Scheduling

This function will be controlled by the physicians from their EWD devices. When a doctor logs-on to the P2P software, and clicks on the Appointment Schedule box on his EWDD, he would be able to view the status of all Exam Rooms. The status will also show the special equipment (if any) in each exam room.

Using his EWDD, the physician will select the patient for his next appointment, and an exam room to examine the patient. This action will mark the exam-room as Occupied, and the name of the patient (to be examined) will begin to flash in the waiting room as well as on the Nurse-station PC. The patient will read his blinking name, follow the signs in the hallway, and go to the exam-room himself. (This function will eliminate the need for a medical assistant to come to the waiting room, call-out the name of the patient, and take him to the exam room.) The medical assistant will go to the exam room and prepare the patient for examination. When the patient is ready to be examined by the doctor, the medical assistant will check a box on the Appointment Schedule screen, indicating Patient Ready status. The doctor will see the same on his EWD device, and go to the exam room to examine the patient.

After the physician finishes examining a patient, he will un-check the box for that particular exam-room. The change of status will be displayed on the waiting room large screen, Front Desk PCs, Nurses Station PC, as well as on all physician EWD devices next to the scheduled appointment.

This function will be beneficial particularly to multi-physician office with multiple exam rooms, where manual scheduling becomes difficult, time consuming and costly.

Automated Insurance Verification

Each morning when the medical office opens, the P2P software will assist the staff members to perform automatic insurance verification (with links to insurance company websites) for all patient appointments for the day. The software will assist in flagging the patients with expired insurance. This function will help the medical practice to collect payments from the patients who do not have valid insurance at the time of service. This will also reduce the overhead cost of the physician, since the office staff does not have to spend time calling the insurance company to verify the insurance information.

Electronic Superbills

The P2P software installed on the Physician's EWD device will replace the paper Superbill with an Electronic Superbill. Since the EWDD is connected to the MOPM/MOIS through the LAN, the physician will have access to all ICD9 diagnosis and CPT procedure codes stored in MOIS. After examining the patient, he will select suitable diagnosis & procedure codes on the Electronic Superbill. After completion, the Superbill data will be uploaded to the local Server within the medical office.

If the physician is away from his main office, at a location where connection to P2P network is not available, the superbill will be stored locally within the EWDD. As soon as he reaches a location where he can connect to the P2P network through private/public network such as Internet (locations like hospital or his branch office), the Superbill data stored in the EWD device will be downloaded to the Server in his main office. A medical office staff member will review and fill-in the incomplete codes, if needed. The completed Superbills will be ready for billing.

Intelligent Electronic Superbills

An Intelligent Electronic Superbill (IES) is created by the physician using an EWD device, and upon completion, it is stored in the local MOIS. As defined by the invention, an IES assists the physician in selecting the most suitable diagnosis codes, and cost effective procedure codes for a patient encounter. The IES is an electronic form which can be custom programmed to meet the needs of any physician. This form can be displayed on a physician's EWD, or any other computer in the medical office in response to a user-request. Since the EWD is connected to the P2P network, a physician can access any information related to a diagnosis code/procedure code stored within the network, including the historical information of all codes used by all other physicians within the network. An IES can be custom programmed such that it automatically searches the P2P network databases, performs certain computations, and presents the resulting information to the physician to assist him in selecting the appropriate codes. Without the P2P network, designing an IES would not be possible.

Automated Electronic Insurance Claims Submission

Since the Superbill is created in electronic format by the physician using an EWD device, and stored in the local MOIS, the P2P software can be programmed to automatically submit the electronic insurance claims to the clearinghouse computer. At present, this operation is performed manually by the medical office staff using the desktop billing software. Automating this function will reduce the labor cost of the medical practice.

Direct Insurance Claims Submission

There are more than 400 insurance companies in the US. Each company uses a different file format for electronic claims. At present, the clearinghouse Server software performs the task of reformatting the electronic claim files sent by the medical offices to make them compatible with each insurance company format. Recently, the HIPAA regulations have created the new standard EDI (electronic Data Interchange) format for electronic claims. The insurance companies have started to adopt the new EDI standard. The P2P software will be designed to be compatible with the new HIPAA EDI standard, which will enable it to automatically submit direct claims to all insurance companies without having the need of any clearinghouse. This function will further reduce the medical office overhead cost.

Automated Insurance Payment Posting

At present, most of the insurance companies send paper EOBs (Explanation of Benefits; also called ERA (Electronic Remittance Advice)) to the medical offices. In the near future, when they adopt the new HIPAA standards, and start sending electronic EOBs, P2P software will extract the insurance payment information from the Electronic EOB file sent by the insurance company, and automatically post payments and adjustments in the local patient database.

At present, the payment posting operation is performed manually by the medical office staff, which is a very time consuming task. Automating this function with the P2P software will significantly reduce the overhead cost of the physician's medical practice.

Check-Out Time Patient Billing

Immediately after the physician completes a Superbill, the P2P software will create the patient financial transaction in real-time. By the time patient reaches the checkout desk, the medical staff will be able to generate a Patient Check-Out Statement to be given to the patient. Based on the insurance information stored in the MOIS, the Check-Out statement will show the patient portion of the bill, along with the portion covered by his insurance policy. This statement will help the medical practice to collect payments from the patients at the time of service, which otherwise, is not possible using the paper Superbills.

Automated Electronic Patient Billing

After the insurance payment is posted in the local patient database within the MOIS, the P2P software will automatically generate a patient invoice (also referred as patient statement) for the remainder amount (which is patient's responsibility), and send it electronically to the patient.

At present, this operation is performed manually by the medical office staff using the desktop billing software, and paper invoices are mailed to the patients. Automating this function will reduce the labor cost of the medical practice.

Patient Self-Bill Payment

Patients will be able to access their accounts information from anywhere in the world by logging to the P2P network, and make payments using their credit cards or Electronic Funds Transfer (EFT). The payment information will be automatically transferred to the medical office MOIS database.

This function will reduce the number of patient phone calls related to billing questions, and reduce the workload of the medical staff thereby reducing the overhead cost. At the same time, it will improve the quality of service and convenience to the patient.

Automated Secure Messages to Patients

At present, the medical offices communicate with the patients using a telephone. Some medical practices have started to use e-mails. Since the information sent through e-mail is not secure, and is vulnerable to viruses, confidential health information cannot be sent using this method.

The P2P network will enable the physicians & the medical office staff to send messages to patients through a secure infrastructure. When a patient logs-in to the P2P network, the P2P software will automatically send saved notifications to the patient. Urgent messages would pop-up on his computer screen. The patient could open other messages at his convenience. The P2P software will allow the physicians to send the following types of messages:

Appointment confirmation/reminders
Recall Appointment messages
Patient Bills (Statements) and late payment notices
Answers to medical questions he asked on-line
Medical articles from the P2P knowledge base specific to each patient's medical condition
Medical alerts specific to each patient's health condition
Advertisements targeted to the health conditions of patient The types of messages sent to patients are not limited to the above examples. Almost any type of message can be added to the above list by custom programming. This secure P2P messaging system will improve the electronic communication and relationships between the physician and the patients. The automated messaging will reduce the medical office workload, and improve the quality of services to the patients, since they will be able to retrieve the messages from anywhere in the world.

Patient Messages and Questions to Physicians

Patients will login to the P2P network, create and send messages for their doctors, or any other medical staff member. Examples of patient messages and questions are as follows:

Related to their previous visits, and/or present medical condition
Patient statements (bills)
Insurance payments (for previous visits of patient)
Request for a referral
Request for a Prescription Refill The types of messages sent by patients are not limited to the above examples. Almost any type of message can be added to the above list by custom programming. The messages & questions will be automatically routed to the specific doctor's (or other staff member's) mailbox. Each message will be assigned a priority level by the patient. Urgent messages will pop-up instantaneously on Office Manager's computer, who would send it to the appropriate physician's EWD device in real-time after screening. Manager/physician would have the ability to delete, or save the messages.

Automated Electronic Referrals

A medical office employee (or a physician using his EWD device) will be able to fill-in the electronic referral form, and send it to the Specialist's medical office Server, or Hospital or any other facility by electronically transferring the information within the P2P network.

This function will facilitate collaboration among physicians/medical offices, and reduce the workload of medical offices at both ends thereby reducing their overhead cost. At the same time, it will help improve the quality of services to patients. At present, a patient makes a phone call to physician's office to request a referral, and the referrals are faxed from one medical facility to another, and it can take up to 3 days to send the referral from a busy medical practice. To avoid this delay, many patients make a trip to the medical office to pick up the referral, and personally take it with them.

Automated Transfer of Patient Health Information

When a referral is electronically transferred from the primary care physician to a specialist, a diagnostic lab, or any other healthcare service facility (which is a member of the P2P network), the P2P software will automatically transfer the needed patient health information in real-time to the medical facility's Server along with the referral information. If the facility already has the patient information, but it is not current, the software will update the information.

This function will facilitate collaboration among physicians/medical offices, and eliminate the manual data entry operation at the specialist's office/medical facility, thereby reducing their overhead labor cost. At the same time, it will improve the quality and convenience of services to the patient, since he won't have to fill-out all the forms again.

On-Request Transfer of Patient Health Information

A physician, or an authorized medical staff member will have the capability to request patient EMRs stored in any other medical office's MOIS within the P2P network. Upon request generated from an EWDD or any other computer, the patient EMRs will automatically get transferred in real-time to the requesting device.

A physician, or any other authorized HC service provider can also request any information related to patient health stored in the CPIS in any P2P data center. After the identity of the requesting user is verified, the information is automatically transferred to the requesting device.

This function will improve the electronic communication among physicians, enable them to collaborate with each other, and eliminate medical office's workload associated with the manual request and transfer of EMRs using telephone and fax machines.

Automated Electronic Prescriptions

A medical office employee (or a physician using his EWD device) will be able to fill-in the electronic prescription form, and send it to the pharmacy's computer (who is a member of the P2P network) by electronically transferring the information.

This function will facilitate collaboration among physicians & HC service providers, and reduce the workload of medical office and pharmacy, thereby reducing their overhead cost. At the same time, it will help improve the quality of services to the patient.

At present, a patient makes a phone call to physician's office to request a prescription refill, or the pharmacy faxes a refill request. The prescriptions are filled manually by the physician/medical staff on a paper form and faxed to the pharmacy. It can take up to 3 days to send the prescription refills from a busy medical practice. To avoid this delay, many patients make a trip to the medical office to pick up the prescription, and personally take it with them.

Electronic Reference Books

Certain types of EWD devices, such as a Tablet PC, are fully functional computers, and are capable of storing electronic version of medical books that are used everyday by physicians. An example of such a book is the Physicians Desk Reference (PDR). Almost every physician uses this reference book to select suitable medicines for a patient's diagnosis codes, and to write prescriptions.

The P2P software installed on an EWD device will include such reference books, and make them a part of the network system. Since the EWD devices have limited storage capacity, a large number of electronic reference books will be stored in the OIS at the central Data Center. The physicians will access these reference books from anywhere using their EWD devices, or any other computer.

Electronic Medical Records (EMRs)

Most of the medical practices and other HC service providers currently store patient health information in non-electronic form on paper, imaging film and photographic paper. The existing patient medical records consist of the following types:

Hand written notes by the physician on Patient charts (paper)

Photocopies (B&W and colored) of documents such as Insurance Card, Employee ID card, Driver's license, Registration Form, and HIPAA documents.

X-Rays on transparency film

Sonograms, Magnetic Resonance Imaging (MRI), Cat Scan and other electronic images The P2P software will have the provision to transform all of the above types of medical records into electronic formats such as text, gray scale images (of hand written notes and X-Rays), and colored images (such as patient's ID card and Driver's license). The staff in the medical office will be able to scan the existing records using a scanner. The scanned images will be attached to the appropriate patient records and stored within the local MOIS as EMRs.

The physician will create new patient charts, as part of EMRs, in his own handwriting using an EWD device. These charts will be temporarily stored in the EWDD, and upon completion transferred to medical office MOIS. A medical typist in the office, or from a remote location anywhere in the world will have the capability to view the handwritten charts, and type the same information using a keyboard. The typed information will be stored in the local MOIS as an EMR. The EMRs stored in any medical office can be transferred and shared with all other physicians within the P2P network.

The main advantage of the natural method of creating EMRs, as disclosed by the invention, is its cost effectiveness. The method is efficient, since the time taken to create EMRs is less than the template-based system. Since a physician's time costs more to the medical practice as compared to the medical typist's time, the method saves money to the medical practice.

The number of errors in converting handwritten notes to typed notes can be reduced to zero in an efficient manner. If the medical typist is unable to read certain words written by the physician, he simply highlights those words, and leaves blank spaces in the typed text. The physician can later review the highlighted words and make the corrections himself, or have it done by a staff member. This error-correction process of the invention is more efficient as compared to the most popular dictation system, where the physician has to playback the serially recorded voice notes in order to make corrections.

Compliance with HIPAA Regulations

The EMRs, along with many other P2P network software functions such as electronic Registration Forms, electronic Medial History forms, electronic Sign-In Sheet, and encrypted data transfer through P2P network system will make the medical office paperless and fully compliant with HIPAA regulations.

Tele-Working by Physicians & Medical Staff

The P2P network system will enable physicians and office staff members to connect to their medical office network and access medical office MOPM/MOIS from remote locations using any computer. Since all patient and business information will be stored in electronic format, they will be able to work from remote locations. This function will eliminate the need to physically come to the office, especially under bad weather conditions, resulting in improved efficiency and reduced overhead cost.

Tele-Examination by Physicians

The P2P network will facilitate physicians to tele-examine patients at their homes (or any other location) from any remote location. The patient will need low cost tele-diagnostic devices such as a Web Cam (a video camera capable of transmitting images through the Internet) and a tele-stethoscope (capable of transmitting sound through the Internet or a private network) etc.

In the past, tele-examination has been limited only to emergency situations at large HC organizations where the physician is located at the main facility, such as a hospital in a city, and the patient is at the branch office in a rural area. A broadband private network connection between the main facility and the remote location enabled the tele-examination process.

However, the P2P network system would enable tele-examination through the public network such as Internet, or any other private network. The tele-examination will be helpful in case of simple ailments (such as ear infection for a small baby) at late hours when the medical offices are closed. Instead of going to the urgent care/emergency room, the patient could be examined in his home by any P2P member physician from anywhere in the world, including physician's home.

Tele-Diagnosis by Physicians

The physicians and lab technicians will have the ability to connect to the MOIS/MOPM from any remote location, and view the images of diagnostic tests such as X-Rays, cat scans, sonograms and cancer test slides. This function will enable the physicians to study the images and send their diagnosis reports from remote locations. Any other physician within the network will be able to retrieve the diagnosis report from anywhere at any time. The patients would also be allowed to view and print their health related reports from anywhere. This function will help improve the efficiency of nation's HC industry, improve the quality of services, and reduce the overhead cost.

Video-conferencing for Physicians

The P2P network system will enable physicians to conduct video-conferences among P2P members. Since most of the independently practicing physicians are over-worked and their time is very valuable, this function will save them travel time, resulting in improved productivity.

Since this function requires higher bandwidth, high-resolution videoconferencing will be feasible to implement within a medical building with multiple medical offices using the Local Area Network. However, the branch offices, or medical office locations where high-speed Wide Area Network connection is not yet available, only low-resolution video-conferencing will be possible.

Tele-Research by Scientists

The research scientists will have the ability to connect to the P2P CPIS from any remote location, and selectively retrieve historical/current HC information of all, or a specific group of patients within a community. Each HC research organization can design and develop its own custom software programs to conduct research on patient data retrieved from the CPIS. The research reports can be shared among HC product and service providers, educational institutes, government agencies and any other authorized users.

This function will help the HC industry to improve the quality of healthcare services nationwide.

Real-Time Community Health Status

The most recent health information of majority of patients (with the exception of patients admitted in the hospitals, or residing in nursing homes) is stored in the medical offices of independently practicing physicians. Since the P2P network will facilitate creation of EMRs, custom software can be developed to extract specific information from medical office MOISs, and to save the same in the CPIS. An authorized healthcare organization (such as Centers for Disease Controls) can access this information in real-time from P2P central data center, and create Community Health Status reports.

This function will help the hospitals and federal government agencies to continually track the health of communities, and monitor the status of infectious diseases.

Medical Practice Website

Now a days, almost every business in the country has a website. However, Most of the independently practicing physicians don't have any website. The P2P network will offer an opportunity to all the member physicians & practices to create their websites, which are linked to each other as a private community. The medical practice website will enable its physicians to advertise their credentials, experience levels, awards, memberships of professional organizations and all other qualifications & strengths that will help them in acquiring new customers (patients).

Having websites for medical practices will be the first step towards transforming the Insurance-Employer controlled healthcare system to a market-driven industry. The physicians will begin to view their practice as a business, and view patients as customers. The patients will begin to realize that they are customers, and view a physician as a service provider who gets paid by the customer. The patients will have the opportunity to look at a number of websites to evaluate, compare and select a medical practice, and a physician of their choice.

Medical Knowledge Base

Each medical practice website will have a comprehensive medical knowledge base for patients. The knowledge base will include medical information specific to the medical specialty about most commonly asked questions by the patients. Preventive care information will also be included in the knowledge base. Adding new information and removing outdated information will regularly be performed on the knowledge database.

Patients will have the freedom to view the knowledge base and get answers to their questions at any time. The knowledge base will also help educate the patients, and reduce the number of phone calls to the medical office resulting in overhead cost savings.

One2One HC Advertising Function

Since the medical office MOIS systems and the CPIS data centers of P2P network contain the information related to the specific medical condition (such as a diagnosis code) of each patient, the P2P software will have the capability to allow the healthcare product suppliers & service providers to send a specific (One) advertisement, and related educational and healthcare information, to a specific (One) patient or physician within the P2P network. The One2One advertisements can also be sent to the physicians' EWD devices at the right time at the right place. For example, when the physician finishes examining a patient, and marks an ICD diagnosis code on his EWD device, the P2P software will display an advertisement on his EWDD about one, or more than one, medicines that are suitable for the treatment related to the diagnosis code. This type of highly targeted advertisements will reduce the marketing cost of the healthcare product suppliers, and service providers. By providing timely information to the physician, the One2One technology will save physician's time to search the most suitable treatment for the medical condition of the patient.

HC Products at Discount Prices

The P2P network system will facilitate patients and other P2P network members to purchase medicines and healthcare products advertised by authorized suppliers through the network system. The patients will be able to remotely access the detailed product information stored in the OIS, compare the products and make the final purchases. Since the sale of products through the P2P system will not involve a retail store, sales staff and other overhead costs unlike a pharmacy, the patients will be able to purchase medicines and other HC products at discounted prices.

Since the products & services listed on the P2P network system will require pre-approval of the physicians, the network will serve as an authentic & reliable source for the patients to purchase healthcare products.

P2P Q-Rating System

A Q-Rating system will be created within the P2P network system to help monitor and control the quality of services provided by the physicians, medical practices and other HC service providers. Each physician, medical practice, and other HC service organizations (hospitals, nursing homes, urgent care clinics, diagnostic labs, pharmacies, insurance companies etc.) will be assigned a Q-Rating. This rating will be computed in real-time by the P2P software based on many factors such as a physician's qualifications, experience level, credentials, number of years in business, and above all, the feedback from the patients. The feedback from other physicians and HC officials who have past experience dealing with a physician/medical practice will be a major factor to compute the Q-Rating of a service provider. All P2P members will have the ability to give feedback by logging to P2P network, and fill-out a simple form by answering questions related to their personal experience with a service provider. The name and other personal information of the P2P member giving feedback will be held confidential by P2P system.

Custom Software Functions

The P2P network system offers the flexibility to add numerous functions in the future to the existing network by developing and installing custom software. The possibilities are end-less and only limited by human imagination.

CONCLUSION

The P2P network system, when completely implemented as the Global Network system, will reduce the total cost of the healthcare industry, and improve the quality of services to the patients. The P2P Network is a system with potential to benefit the entire mankind.

What is claimed as new, and desired to be secured by a U.S. Patent is:

1. A Physician to Patient (P2P) system for real-time electronic communication, transfer of patient health information, and collaboration among healthcare user groups and P2P members including independently practicing physicians, scientists, lab technicians, and patients, the system comprising:
   α. a network connected to a plurality of healthcare user computers and a plurality of patient computers located remotely from each other
   β. the network of computers configured to perform:
      i. authorizing and scheduling a patient using a series of questions initiated by the P2P system that describes the patient's health condition in an appointment request and submitting the appointment request to a medical staff member for review;

ii. a remote patient registration wherein the patient logs in using a patient ID and password and inputs related healthcare information, including at least, patient's personal data, insurance policy information, and medical history into a patient computer, the remote patient registration sent to a healthcare provider computer using a P2P central server;

iii. an electronic patient sign-in sheet wherein the patient signs in to be listed on an electronic waiting room list;

iv. an automated exam room scheduling function for the healthcare provider to view the status of all exam rooms;

v. an automated insurance verification for performing verification for all patient appointments for a particular day;

vi. displaying an intelligent electronic superbill to assist the healthcare provider in selecting diagnosis codes and cost effective procedure codes after the patient has been examined by accessing information related to a diagnosis code/procedure code stored within the network and automatically searching the P2P network databases to present the resulting information to the healthcare provider;

vii. an automated electronic payment posting in a medical office database after extracting insurance payment information from a electronic explanation of benefits file sent by an insurance company;

viii. an automated electronic insurance claims submission to submit electronic insurance claims to a clearinghouse computer or directly to an insurance company computer;

ix. a check-out time patient billing function for generating a check-out statement after the healthcare provider has completed a superbill, the check-out statement containing a patient payment portion and a portion covered by the patient's insurance policy, the patient's statement for sending electronically to the patient;

x. an automated transfer of secure electronic messages between the healthcare providers and patients;

xi. an electronic referral form for electronically transferring information to a specialist's facility including at least one of: a medical office server and a hospital;

xii. an on-request/automated transfer of electronic medical records, electronic referrals, electronic prescriptions and related patient information among healthcare service providers and patients;

xiii. a storage of electronic reference books accessible by P2P members;

xiv. electronic communication and collaboration between physicians and office staff members;

xv. providing authorized users, including at least physicians, research scientists, and lab technicians to access the network to conduct research, prepare, store, view, and print research reports;

xvi. a conversion of paper medical records to electronic medical records;

xvii. the patient remotely accessing detail healthcare product information and the ability to purchase a plurality of healthcare products;

xviii. the healthcare provider to conducting video conferences among P2P members, wherein video conferencing includes enabling the physician to tele-examine the patient using a plurality of devices including a web camera;

xix. enabling healthcare providers and lab technicians to tele-diagnosis by allowing said physicians and lab technicians the ability to view images from diagnostic tests and send diagnosis reports;

xx. allowing the patient the ability to view and print their healthcare related information including at least one of: medical bill, diagnosis report, and electronic medical record;

xxi. allowing the patient access to their billing account, wherein the patient is able to view and pay their medical bill;

xxii. a q-rating system to provide feedback as to the quality of healthcare services to patients.

2. The Physician to Patient (P2P) system of claim 1, further comprising: a One2One healthcare advertisement system that enables authorized healthcare product suppliers and service providers to send an advertisement to the patient or the healthcare provider based on a specific medical condition of the patient; and the P2P network members, including at least one healthcare provider and one patient, can view the advertisement and any other One2One healthcare information.

3. The Physician to Patient (P2P) system of claim 1, further comprising: a creation of electronic medical records by healthcare providers written in their own handwriting.

* * * * *